(12) United States Patent
Chen et al.

(10) Patent No.: US 10,768,135 B2
(45) Date of Patent: Sep. 8, 2020

(54) OXIDIZING GAS DETECTION METHOD AND APPARATUS THEREOF

(71) Applicant: INDUSTRIAL TECHNOLOGY RESEARCH INSTITUTE, Hsinchu (TW)

(72) Inventors: I-Cherng Chen, Hsinchu (TW); Pi-Guey Su, Hsinchu (TW); Hong-Ci Syu, Miaoli County (TW); Hui-Yu Cho, Taichung (TW); Pin-Chou Li, Hsinchu (TW); Jian-Hong Wu, Nantou County (TW); Ren-Der Jean, Hsinchu (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 137 days.

(21) Appl. No.: 15/855,933

(22) Filed: Dec. 27, 2017

(65) Prior Publication Data

US 2019/0195823 A1   Jun. 27, 2019

(51) Int. Cl.
*G01N 27/30* (2006.01)
*G01N 27/27* (2006.01)
(Continued)

(52) U.S. Cl.
CPC ........... *G01N 27/27* (2013.01); *G01N 27/305* (2013.01); *G01N 27/407* (2013.01);
(Continued)

(58) Field of Classification Search
CPC .................................................. G01N 27/305
See application file for complete search history.

(56) References Cited

U.S. PATENT DOCUMENTS 7,069,769 B2    7/2006  Kung
2006/0000259 A1*  1/2006  Rothschild ........... G01N 27/125
                                                              73/31.06
(Continued)

FOREIGN PATENT DOCUMENTS

CN    101458221 B    8/2012
CN    106053376 A   10/2016
(Continued)

OTHER PUBLICATIONS

Xu et al., "Light-Activated Metal Oxide Gas Sensors: A Review", Micromachines 2017, 8, 333 (Year: 2017).*
(Continued)

*Primary Examiner* — Alexander S Noguerola
(74) *Attorney, Agent, or Firm* — Maschoff Brennan

(57) ABSTRACT

An oxidizing gas detection method and an apparatus thereof are provided for trace oxidizing gas detection. The detection method includes the following steps. First, perform an electroreduction reaction and a photoreduction reaction simultaneously to a metal oxide in which nanoconductors are distributed. Next, stop the electroreduction reaction and the photoreduction reaction, and read a resistance of the reduced metal oxide by applying a first pulse-width modulation signal. Next, provide an oxidizing gas to the reduced metal oxide, and photo-catalyze a redox reaction between the oxidizing gas and the reduced metal oxide. Next, read a resistance of the oxidized metal oxide by applying a second pulse-width modulation signal. Next, converse a concentration of the oxidizing gas according to a ratio of the resistance of the oxidized metal oxide and the resistance of the reduced metal oxide.

24 Claims, 12 Drawing Sheets

(51) Int. Cl.
G01N 27/407 (2006.01)
G01N 27/406 (2006.01)
G01N 33/00 (2006.01)
(52) U.S. Cl.
CPC ..... *G01N 27/4065* (2013.01); *G01N 33/0037* (2013.01); *G01N 33/0039* (2013.01)

(56) References Cited

U.S. PATENT DOCUMENTS

| | | | |
|---|---|---|---|
| 2008/0110241 | A1 | 5/2008 | Rothschild et al. |
| 2010/0077840 | A1 | 4/2010 | Srivastava et al. |
| 2011/0259080 | A1 | 10/2011 | Ratcliffe et al. |
| 2012/0062895 | A1 | 3/2012 | Rao |
| 2017/0016867 | A1 | 1/2017 | Chung |
| 2017/0307557 | A1 | 10/2017 | Muraoka et al. |

FOREIGN PATENT DOCUMENTS

| | | |
|---|---|---|
| CN | 106596652 A | 4/2017 |
| CN | 104569061 B | 6/2017 |
| CN | 106145905 A | 10/2018 |
| TW | 200525139 A | 8/2005 |
| TW | I433270 B | 4/2014 |

OTHER PUBLICATIONS

CRC Handbook of Chemistry and Physics 97th Edition, 2016-2017, pp. 5-78 to 5-84. (Year: 2017).*

Maria Hepel, "Electrochromic WO3 Films: Nanotechnology Experiments in Instrumental Analysis and Physical Chemistry Laboratories," Journal of Chemical Education vol. 85 No. 1 Jan. 2008, pp. 125-127 (Year: 2008).*

Shuchi Chao, "Electrical Characteristics of Glucose-Sensitve Diode Arrays Based on WO3 and IrO2 for Microsensor Applications," Jpn. J. Appl. Phys. vol. 42(2003) pp. L1337-L1339 (Year: 2003).*

Trogadas et al., "Pt/C-WO3 Electrocatalysts for Degradation Mitigation in Polymer Electrolyte Fuel Cells," Journal of the Electrochemical Society, 155 (7) B6960-B703 (2008) (Year: 2008).*

Comini et al., Light Enhanced gas sensing properties of indium oxide and tin dioxide sensors, Sensors and Actuators B 65 (2000) 260-263 (Year: 2000).*

Fabbri et al., "Chemoresistive properties of photo-activated thin and thick ZnO films," Sensors and Actuators B: Chemical 222 (2016) 1251-1256 (Year: 2016).*

Chen et al., "A Comparative study on UV light activated porous TiO2 and ZnO film sensors for gas sensing at room temperature," Ceramics International 38 (2013) 503-509 (Year: 2013).*

Trawka et al., "UV-Light-Induced Fluctuation Enhanced Sensing by WO3-Based Gas Sensors," IEEE Sensors Journal vol. 16, No. 13, Jul. 1, 2016, 5152-5159 (Year: 2016).*

Zhang et al., Room temperature responses of visible-light illuminated WO3 sensors to NO2 in sub-ppm range, Sensors and Actuators B 181 (2013) 395-401 (Year: 2013).*

A. I. Gavrilyuk, "Photoinjection of Hydrogen in Solids," Ionics 4 (1998), 372-382 (Year: 1998).*

Su, P.G. And Pan, T.-T., "Fabrication of a room-temperature NO2 gas sensor based on WO3 films and WO3/MWCNT nanocomposite films by combining polyol process with metal organic decomposition method," Materials Chemistry and Physics, vol. 125, Issue 3, pp. 351-357 (Feb. 15, 2011).

Espid, E., and Taghipour, F., "Development of highly sensitive ZnO/In2O3 composite gas sensor activated by UV-LED," Sensors and Actuators B: Chemical, vol. 241, pp. 828-839 (Mar. 31, 2017).

Trawka, M.P., et al., "UV-Light-Induced Fluctuation Enhanced Sensing by WO3-Based Gas Sensors," IEEE Sensors Journal, vol. 16, No. 13, pp. 5152-5159 (Jul. 1, 2016).

Zhang. C., et al., "Room temperature responses of visible-light illuminated WO3 sensors to NO2 in sub-ppm range," Sensors and Actuators B: Chemical, vol. 181, pp. 395-401 (May, 2013).

Taiwanese Notice of Allowance issued in corresponding application No. 106145905, dated Oct. 8, 2018.

* cited by examiner

OXIDIZING GAS DETECTION METHOD AND APPARATUS THEREOF

TECHNICAL FIELD

This invention relates to a method and an apparatus for detecting concentration of an oxidizing gas, and more particularly to a method and an apparatus for detecting concentration of the trace oxidizing gas.

BACKGROUND

The concentration of oxidizing gases in the air, such as the concentration of nitrogen dioxide or ozone, is one of several indicators for assessing the degree of air pollution. The main sources of oxidizing gases in the air are vehicle exhaust and factory exhaust. Recent researches show that excessive concentrations of oxidizing gases in the air can cause adverse effects on the respiratory system of the human body, such as irritation of the respiratory tract and reduction of pulmonary function, and even worsen the conditions of chronic lung diseases such as asthma, chronic bronchitis and emphysema. Therefore, with the increasing emphasis on air pollution prevention and control, the requirement for real-time monitoring of the concentration of oxidizing gases in the air also increases accordingly.

Although the conventional oxidizing gas detecting apparatus has the advantages of high sensitivity and high accuracy, it has the disadvantages of bulky size, complex structure expensive price, and is not suitable for real-time monitoring of environmental gases. The commonly used real-time monitoring apparatus for environmental gases is a metal oxide semiconductor detector. The metal oxide semiconductor detector has the advantages of small size, low cost, and good weathering resistance, but it also has the disadvantage that the detecting result is easily interfered by the reducing gas. In addition, the commonly used metal oxide semiconductor detector needs a high temperature such as 200 degrees Celsius and above to perform the concentration detection for trace gases, resulting the interference of the reducing gas being more obvious. Therefore, in order to satisfy the increasing demand of real-time monitoring of the concentration of oxidizing gas, it is necessary to develop the oxidizing gas detecting apparatus which has the ability to detect concentration of the trace gases and the detection result is not easily affected by the concentration of the reducing gas.

SUMMARY

This invention relates to a method and an apparatus for detecting concentration of an oxidizing gas, to satisfy the requirement of real-time monitoring of the concentration of trace oxidizing gas, and to solve the problem that the detection result is easily interfered by the reducing gas.

The method for detecting the concentration of the oxidizing gas according to this invention comprises: providing a gas detecting module with the gas detecting module comprising a metal oxide and a plurality of nanoconductors, wherein the plurality of nanoconductors are distributed in the metal oxide; performing an electroreduction reaction and a photoreduction reaction simultaneously to the metal oxide; stopping the electroreduction reaction and the photoreduction reaction to the metal oxide; applying a first pulse-width modulation signal for reading an reduction-state resistance of the reduced metal oxide; providing the oxidizing gas to the reduced metal oxide; performing a redox reaction by photo-catalyzing the oxidizing gas and the reduced metal oxide; applying a second pulse-width modulation signal for reading an oxidation-state resistance of the oxidized metal oxide; and calculating the concentration of the oxidizing gas according to a ratio of the oxidation-state resistance to the reduction-state resistance.

The apparatus for detecting the concentration of the oxidizing gas according to this invention comprises a gas detecting module comprising a metal oxide and a plurality of nanoconductors, wherein the plurality of nanoconductors are distributed in the metal oxide, and the metal oxide is configured to perform a redox reaction with the oxidizing gas; a light module comprising a photoreducing light and at least one photocatalytic light, wherein the photoreducing light is configured to irradiate and drive the metal oxide to be photoreduced, and said at least one photocatalytic light is configured to catalyze a reaction of the oxidizing gas with the reduced metal oxide so that the oxidizing gas is reduced; and a control module electrically connected to the gas detecting module and the light module, wherein the control module is configured to drive the metal oxide to be electroreduced and photoreduced in a constant voltage mode, and to detect a reduction-state resistance of the reduced metal oxide and an oxidation-state resistance of the oxidized metal oxide in a pulse-width modulation mode, wherein the reduction-state resistance and the oxidation-state resistance are configured to calculate a concentration of the oxidizing gas.

According to the method for detecting concentration of an oxidizing gas and apparatus thereof, by firstly performing an electroreduction reaction and a photoreduction reaction simultaneously to the metal oxide; then stopping the electroreduction reaction and the photoreduction reaction to the metal oxide; then applying a first pulse-width modulation signal for reading an reduction-state resistance of the reduced metal oxide; then providing the oxidizing gas to the reduced metal oxide; then performing a redox reaction by photo-catalyzing the oxidizing gas and the reduced metal oxide; then applying a second pulse-width modulation signal for reading an oxidation-state resistance of the oxidized metal oxide, the sensitivity of the method for detecting concentration of an oxidizing gas is improved. Moreover, through performing a redox reaction by photo-catalyzing the oxidizing gas and the reduced metal oxide, the detection result of the concentration of the oxidizing gas is not easily interfered by the reducing gas. In this way, the method for detecting concentration of an oxidizing gas and apparatus thereof as set forth above can satisfy the requirement of real-time monitoring of the concentration of trace oxidizing gas, and can solve the problem that the detection result is easily interfered by the reducing gas.

The above description of the summary of this invention and the description of the following embodiments are provided to illustrate and explain the spirit and principles of this invention, and to provide further explanation of the scope of this invention.

DETAILED DESCRIPTION

The detailed features and advantages of the invention will be described in detail in the following description, which is intended to enable any person having ordinary skill in the art to understand the technical aspects of the present invention and to practice it. In accordance with the teachings, claims and the drawings of the invention, any person having ordinary skill in the art is able to readily understand the objectives and advantages of the invention. The following embodiments illustrate the invention in further detail, but the scope of the invention is not limited by any point of view.

Figure 1:
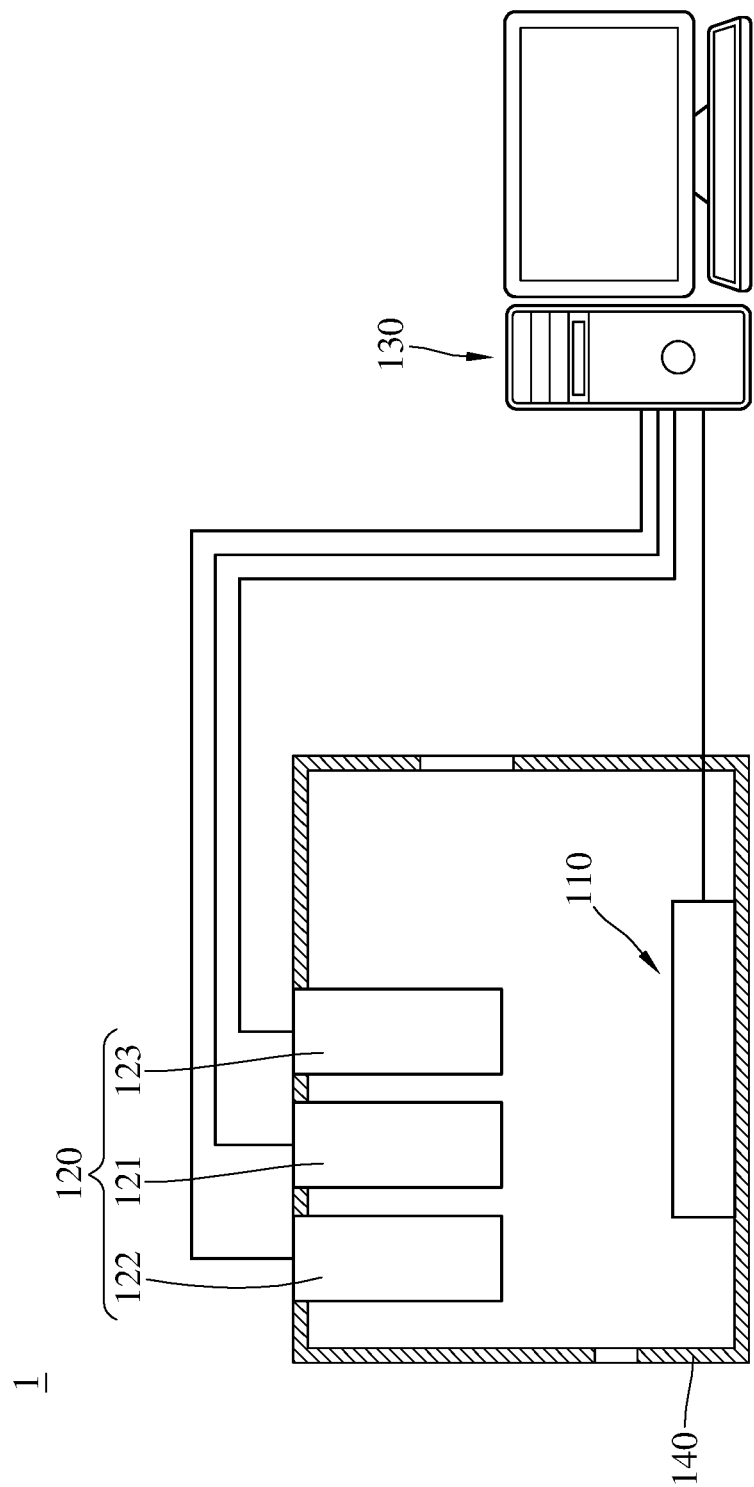
FIG. 1 is a schematic view of an apparatus for detecting concentration of an oxidizing gas according to an embodiment of the present invention.
Figure 2:
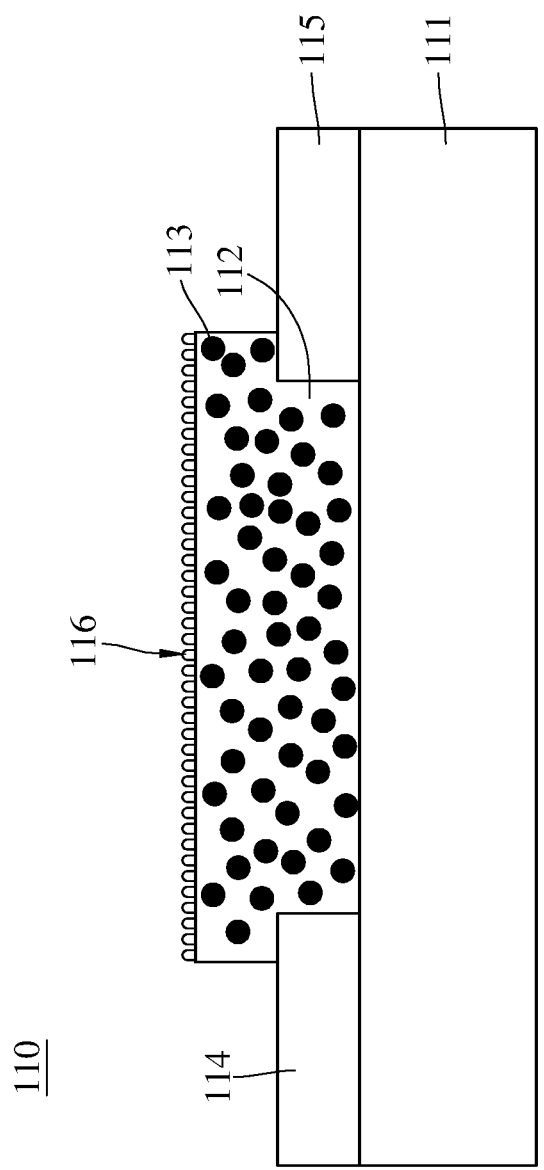
FIG. 2 is a schematic view of a gas detecting module of the apparatus for detecting concentration of an oxidizing gas shown in FIG. 1.
Figure 3:
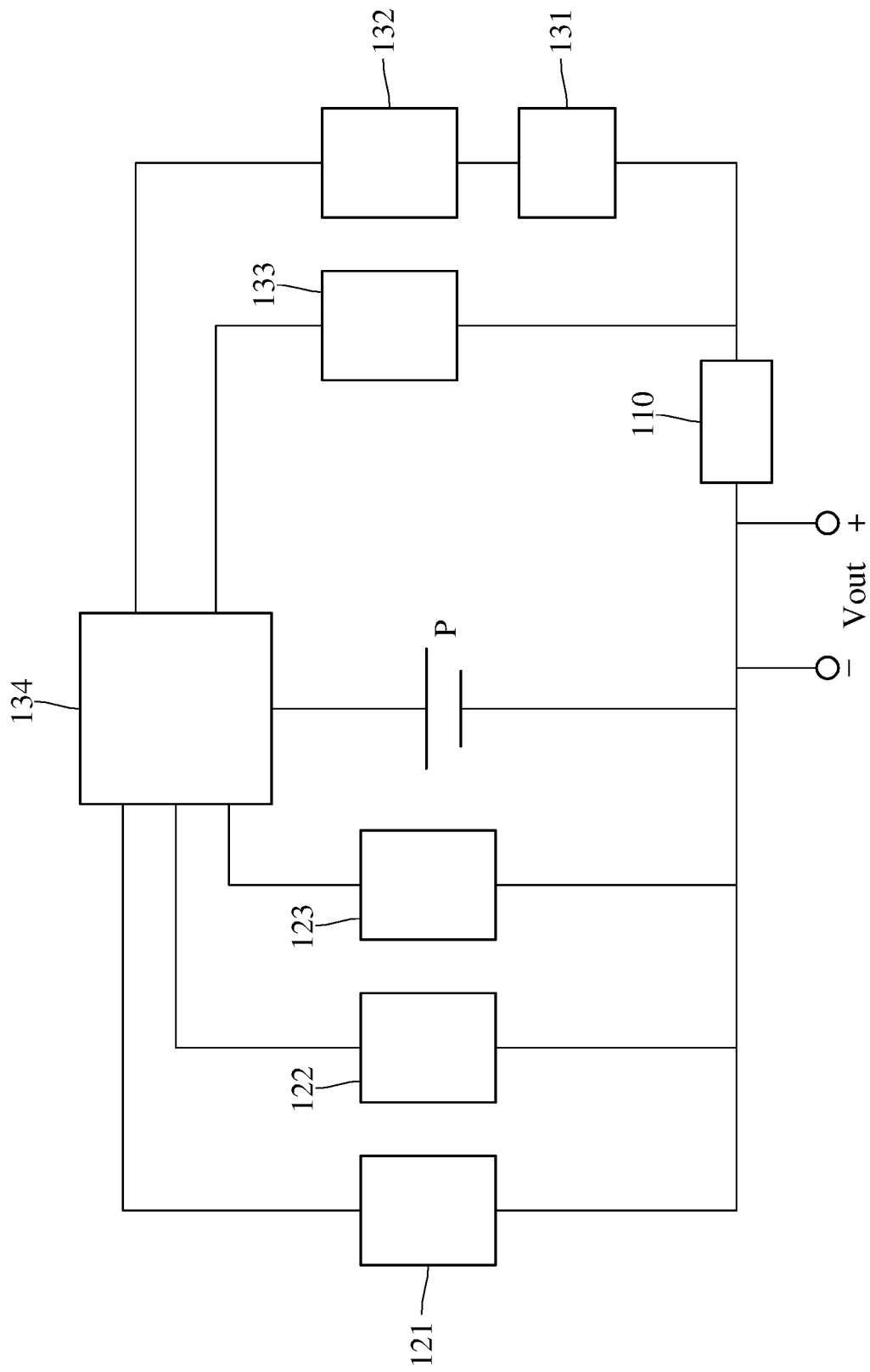
FIG. 3 is a block diagram of the apparatus for detecting concentration of an oxidizing gas shown in FIG. 1.

First, the apparatus for detecting concentration of an oxidizing gas according to an embodiment of the present invention will be described here, please refer to FIG. 1-4. FIG. 1 FIG. 1 is a schematic view of an apparatus for detecting concentration of the oxidizing gas according to an embodiment of the present invention, FIG. 2 is a schematic view of a gas detecting module of the apparatus for detecting concentration of the oxidizing gas shown in FIG. 1, FIG. 3 is a block diagram of the apparatus for detecting concentration of the oxidizing gas.

The apparatus 1 for detecting concentration of the oxidizing gas comprises a gas detecting module 110, a light module 120, a control module 130 and a casing 140. The gas detecting module 110, the light module 120, and the control module 130 are disposed inside the casing 140. The gas detecting module 110 electrically connects to the light module 120 via the control module 130.

The gas detecting module 110 comprises a substrate 111, a metal oxide 112, a plurality of nanoconductors 113, a first electrode 114, a second electrode 115, and a nano-metal catalyst layer 116. The substrate 111 is adapted to carry the metal oxide 112, the substrate's material is such as ceramic, high-molecular material, or glass.

The metal oxide 112 is disposed on the substrate 111. The metal oxide 112 and the oxidizing gas perform a redox reaction when the metal oxide 112 contacts with the oxidizing gas. For example, when the metal oxide 112 contacts with the nitrogen dioxide, the metal oxide 112 and the nitrogen dioxide can perform the redox reaction as shown in chemical equation (1)

$$H_yMO_{3-x}+yNO_2 \leftrightarrow MO_{3-x}+yH^++yNO_2^-$$ Equation (1)

During the redox reaction performing by the metal oxide 112 and the oxidizing gas, the proportion of reduced metal oxide in the entire metal oxide can increase by applying a voltage to the metal oxide 112 or light having a wavelength matched to the metal oxide energy gap.

The nanoconductors 113 is such as the nanocarbon material with sp2 hybrid orbital or the conductive high-molecular material. The nanocarbon material comprises carbon nanotube, graphene, and nano-fullerene/nano-onion. The conductive high-molecular material comprises polyacetylene, polythiophene (PT), polypyrrole (PPY), polyaniline (PANI), poly(3,4-ethylenedioxythiophene)-poly(styrenesulfonate) (PEDOT-PSS), and 3-hexylthiophene (P3HT).

The first electrode 114 and the second electrode 115 are disposed on the substrate 111. The first electrode 114 and the second electrode 115 are respectively connected to two opposite sides of the metal oxide 112. The first electrode 114 and the second electrode 115 are configured to apply voltages to the metal oxide 112 for increasing the proportion of reduced metal oxide 112 (HyMOx) in the entire metal oxide 112. The first electrode 114 and the second electrode 115 are also configured to apply voltages to the metal oxide 112 for reading the resistance value of the metal oxide 112. The voltage applied by the first electrode 114 and the second electrode 115 is such as 5 to 10 volts when the metal oxide 112 is reduced.

In the apparatus 1 for detecting concentration of the oxidizing gas of this embodiment, the metal oxide 112 only electrically connects directly to the first electrode 114 and the second electrode 115. As set forth above, compared to the conventional apparatus for detecting a concentration of the oxidizing gas adopting two different sets of electrodes separately to apply voltages to the metal oxide to perform the electroreduction reaction and to read the resistance value of the metal oxide, the apparatus 1 for detecting concentration of the oxidizing gas of this embodiment has the advantages of simple structure, low manufacturing cost and easy miniaturization by using a set of electrodes for both electroreduction and resistance reading.

The nano-metal catalyst layer 116 is disposed on a surface far from the substrate 111 of the metal oxide 112. The nano-metal catalyst layer 116 is configured to catalyze the oxidizing gas and the metal oxide 112 to perform the redox reaction. The nano-metal catalyst layer 116 is such as the mixture of gold and silver, gold, silver or palladium. The gas detecting module 110 comprises the nano-metal catalyst layer 116, however, this is not a limitation of the present invention. In other embodiments, the gas detecting module 110 does not comprise the nano-metal catalyst layer 116.

The light module 120 comprises a photoreducing light 121 and two photocatalytic lights 122, 123. The photoreducing light 121 is configured to irradiate and drive the metal oxide 112 to be photoreduced. Two photocatalytic lights 122, 123 are configured to catalyze the oxidizing gas and the reduced metal oxide to perform the redox reaction so that the oxidizing gas will be reduced. The photoreducing light 121 is the light with a wavelength of 254 to 430 nanometers, for example, a ultraviolet light with a wavelength of 254 nanometers, a ultraviolet light with a wavelength of 365 nanometers, or a blue light. The wavelengths of the photocatalytic lights 122, 123 range from 550 to 950 nanometers, and two photocatalytic lights have different wavelengths, for example, one is a near-infrared light with a wavelength of 850 nanometers while another one is a visible light with a wavelength of 950 nanometers. In the apparatus 1 for detecting concentration of the oxidizing gas of this embodiment, the number of the photocatalytic lights are two, however, this number is not the limitation. In the apparatuses for detecting concentration of the oxidizing gas of other embodiments, the photocatalytic light is a composite light source that can emit the composite light with different wavelengths or a monochromatic light.

The control module 130 is, for example but not limited to, a data processing apparatus such as a computer, and the control module 130 comprises a pulse-width modulator 131 electrically connecting to the gas detecting module 110, a first voltage regulator 132, a second voltage regulator 133, and a controller 134 electrically connecting to the gas detecting module 110 and the light module 120. The control module 130 is configured to drive the metal oxide 112 to be electroreduced and photoreduced in a constant voltage mode, and to detect a reduction-state resistance of the reduced metal oxide and 112 an oxidation-state resistance of the oxidized metal oxide 112 in a pulse-width modulation mode. In detail, the gas detecting module 110 electrically connects to a power source P through the controller 134 in the constant voltage mode, and the controller 134 instructs the first voltage regulator 132 and the second voltage regulator 133 to maintain the voltages of the first electrode 114 and the second electrode 115 to perform the electroreduction of the metal oxide 112, meanwhile, the controller 134 instructs the photoreducing light 121 of the light module 120 to irradiate to perform the photoreduction of the metal oxide 112. The gas detecting module 110 electrically connects to the power source P through the controller 134 and the pulse-width modulator 131 in the pulse-width modulation mode. The controller 134 instructs the pulse-width modulator 131 to convert the voltage signal outputted by the power source P to the pulse-width modulation signals with a specified pulse width, so the reduction-state resistance of the reduced metal oxide 112 and the oxidation-state resistance of the oxidized metal oxide 112 can be read for multiple times. The ratio of the reduction-state resistance and the oxidation-state resistance is configured to calculate the concentration of the oxidizing gas.

Figure 4:
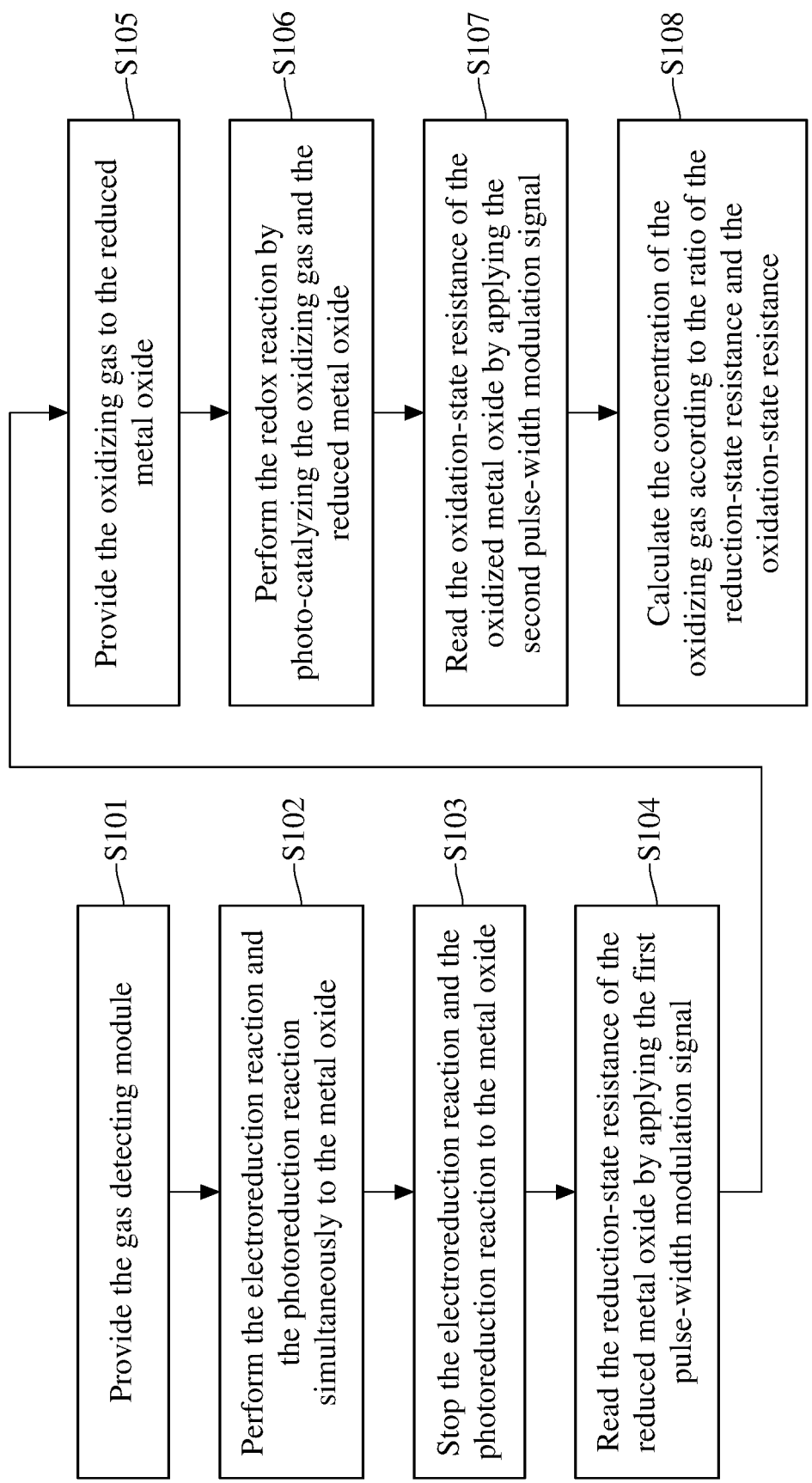
FIG. 4 is a flowchart of a method for detecting concentration of an oxidizing gas according to an embodiment of the present invention.
Figure 5:
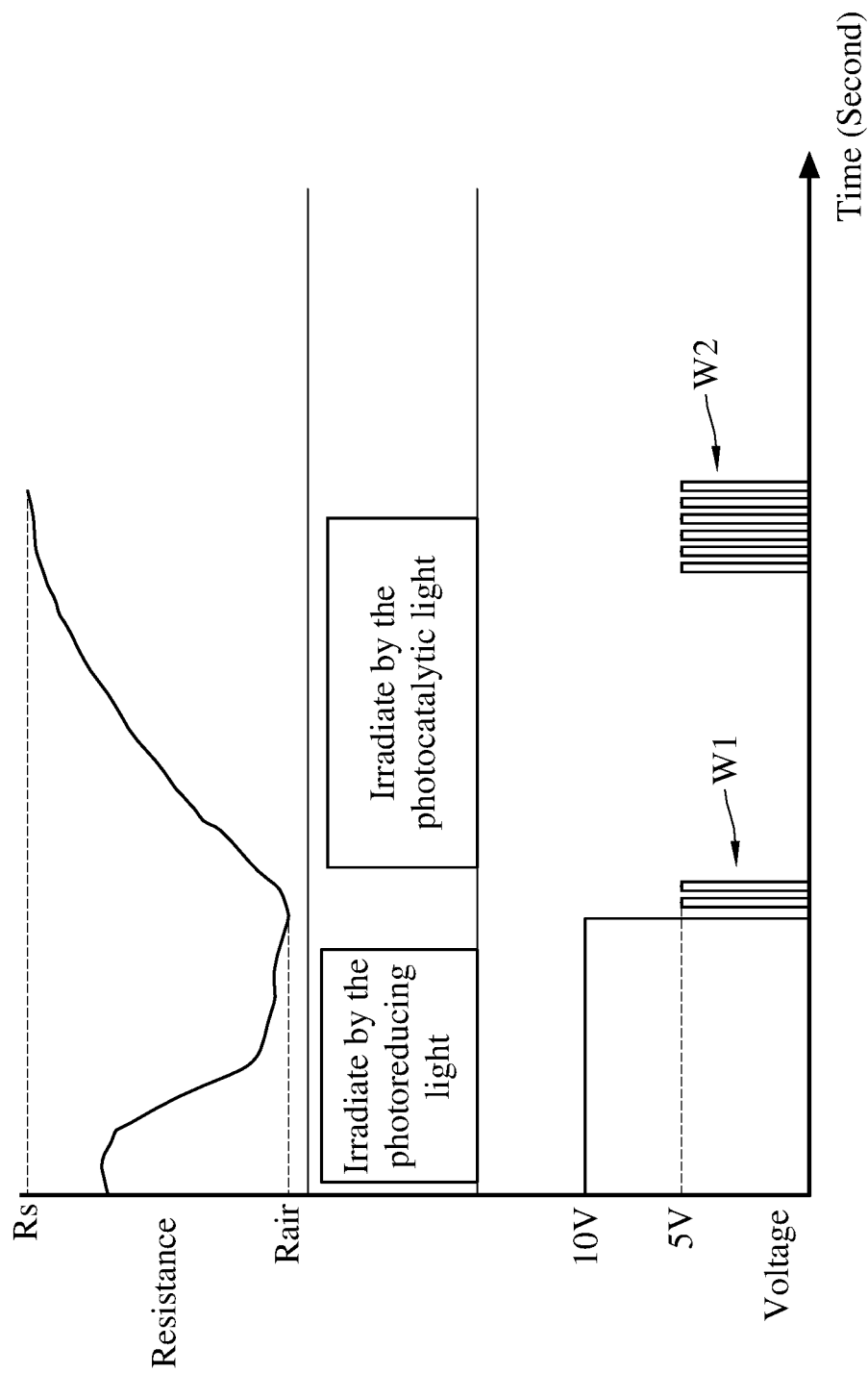
FIG. 5 is a schematic diagram showing the applied voltage, the applied light and the measured resistance versus the variation of time when adopting the method for detecting concentration of an oxidizing gas according to an embodiment of the present invention to perform the detection.

The method for detecting concentration of an oxidizing gas will be described hereinafter. Please refer to FIG. 4 and FIG. 5. FIG. 4 is a flowchart of a method for detecting concentration of an oxidizing gas according to an embodiment of the present invention. FIG. 5 is a schematic diagram showing the applied voltage, the applied light and the measured resistance versus the variation of time when adopting the method for detecting concentration of an oxidizing gas according to an embodiment of the present invention to perform the detection. The method for detecting concentration of an oxidizing gas comprises step S101-S108.

First, the execution of the step S101 is to provide the gas detecting module comprising the metal oxide and the nano-conductors. In this embodiment, the apparatus 1 for detecting concentration of an oxidizing gas will be provided in step S101, and said apparatus 1 for detecting concentration of an oxidizing gas comprises the required gas detecting module 110.

Next, the execution of the step S102 is to perform the electroreduction reaction and the photoreduction reaction simultaneously to the metal oxide 112 of the gas detecting module 110. In this embodiment, the control module 130 of the apparatus 1 for detecting concentration of an oxidizing gas simultaneously activates the first electrode 114 and the second electrode 115 of the gas detecting module 110, and the photoreducing light 121 of the light module 120. Meanwhile, the controller 134 of the control module 130 instructs the first voltage regulator 132 and the second voltage regulator 133 to maintain the voltages of the first electrode 114 and the second electrode 115 in a constant value ranging from 5 to 10 volts (such as the voltages keeps at 10V), so that the gas detecting module 110 is in a constant-voltage state. Maintaining the voltages of the first electrode 114 and the second electrode 115 at 5 volts to 10 volts helps to enhance the efficiency of reducing the metal oxide 112.

As shown in FIG. 5, in the constant-voltage state, the first electrode 114 and the second electrode 115 apply a fixed voltage to the metal oxide 112 for a period of time, so that the metal oxide 112 in the oxidation state ($MO_x$) is reduced to reduced state ($H_yMO_x$), thereby reducing the resistance of the metal oxide 112. Meanwhile in the constant-voltage state, the photoreducing light 121 irradiates the metal oxide 112 with ultraviolet light or blue light to further enhance the reduction efficiency of the metal oxide 112. During the photoreduction reaction, the photoreducing light 121 irradiates the metal oxide 112 with a light having a wavelength of 254 nanometers to 430 nanometers for about 0.1 to 5 minutes, so that the metal oxide 112 can be reduced with appropriate efficiency and with less energy consumption.

Next, the execution of the step S103 is to stop performing the electroreduction reaction and the photoreduction reaction to the metal oxide 112. In this embodiment, the control module 130 turns off the first electrode 114, the second electrode 115, and the photoreducing light 121. In detail, the reaction rate of the electroreduction is usually slower than that of the photoreduction, therefore in this embodiment, the photoreduction reaction to the metal oxide 112 will be stopped first, then the electroreduction reaction to the metal oxide 112 will be stopped after 0.1 seconds to 5 minutes.

Next, the execution of the step S104 is to read the reduction-state resistance Rair of the reduced metal oxide 112 by applying the first pulse-width modulation signal W1. As shown in FIG. 5, the gas detecting module 110 is switched from the constant-voltage mode to the pulse-width modulation mode by the control module 130 so that the voltages of the first electrode 114 and the second electrode 115 can be converted into periodic signals to generate the first pulse-width modulation signal W1. Using the first pulse-width modulation signal W1 to read the resistance value of the metal oxide 112 helps to prevent the metal oxide 112 from being reduced during the measurement because the voltage-applying time is too long, the reliability of the read resistance can be further ensured. Moreover, the applied voltage of the first pulse-width modulation signal W1 is 3 to 7 volts (for example, 5 volts), the frequency is 5 to 15 hertz (for example, 10 hertz), and the applying time is 0.1 milliseconds to 1000 milliseconds (for example, 100 milliseconds), the above configurations help to successfully read the reduction-state resistance Rair of the metal oxide 112 with less energy consumption. In this embodiment, the resistance value of the reduced metal oxide 112 can be read for a plurality of times to obtain the reduction-state resistance Rair, for example, calculate an arithmetic average from a plurality of measured resistance values as the reduction-state resistance Rair of the metal oxide 112.

Next, the execution of the step S105 is to provide the oxidizing gas to the reduced metal oxide 112. In this embodiment, the oxidizing gas is introduced from the opening of the side wall of the casing 140 so that the oxidizing gas diffuses inside the casing 140 and contacts with the metal oxide 112. The oxidizing gas is, for example but not limited to, nitrogen dioxide or ozone.

Next, the execution of the step S106 is to photo-catalyze the oxidizing gas and the reduced metal oxide 112 for performing the redox reaction. As shown in FIG. 5, the control module 130 activates the photocatalytic light 122, 123 of the light module 120 to irradiate the reduced metal oxide 112, so that the oxidizing gas reacts with the metal oxide 112, and the metal oxide in reduction state ($H_yMO_x$) can be further oxidized to oxidation state ($MO_x$) again. The photocatalytic light 122, 123 irradiate a contact surface of the reduced metal oxide 112 with the oxidizing gas with light having a wavelength of 550 nanometers to 950 nanometers. In this embodiment, the photocatalytic light 122, 123 are respectively a yellow light with a wavelength of 590 nanometers and a near-infrared light with a wavelength of 850 nanometers, and the metal oxide 112 is photocatalyzed with the two-color composite light.

Next, the execution of the step S107 is to apply a second pulse-width modulation signal W2 for reading an oxidation-state resistance Rs of the oxidized metal oxide 112. As shown in FIG. 5, the control module 130 changes the voltage periods of the first electrode 114 and the second period 115 so that the gas detecting module 110 can generate the second pulse-width modulation signal W2. Using the second pulse-width modulation signal W2 to read the resistance value of the metal oxide 112 helps to prevent the metal oxide 112 from being reduced during the measurement because the voltage-applying time is too long, the reliability of the read resistance can be further ensured. Moreover, the applied voltage of the second pulse-width modulation signal W2 is 3 to 7 volts (for example, 5 volts), the frequency is 5 to 1000 hertz (for example, 10 hertz), and the applying time is 0.1 milliseconds to 1000 milliseconds (for example, 500 milliseconds), the above configurations help to successfully read the oxidation-state resistance Rs of the metal oxide 112 with less energy consumption. In this embodiment, the resistance value of the oxidized metal oxide 112 can be read for a plurality of times to obtain the oxidation-state resistance Rs, for example, calculate an arithmetic average from a plurality of measured resistance values as the oxidation-state resistance Rs of the metal oxide 112.

Next, the execution of the step S108 is to calculate the concentration of the oxidizing gas according to the oxidation-state resistance Rs and the reduction-state resistance Rair. In this embodiment, the ratio of the oxidation-state resistance Rs and the reduction-state resistance Rair can be outputted to a computer (not depicted) and the ratio is compared with a database stored in the computer to obtain the concentration of the oxidizing gas.

Instead of using a heating method to react a metal oxide 112 with an oxidizing gas, the method for detecting concentration of an oxidizing gas in this embodiment reduces and oxidizes the metal oxide 112 by photoreduction and photocatalytic method, therefore, step S106 can be performed at a room temperature so that the detection result of the concentration of the oxidizing gas is not easily interfered by the reducing gas.

In the step S102, performing the photoreduction reaction by the photoreducing light 121 with a wavelength of 254 nanometers to 430 nanometers can efficiently reduce the metal oxide 112. Please refer to FIG. 6, which is a schematic view of the reduction-state resistance obtained by the photoreduction with different lights according to the method for detecting concentration of an oxidizing gas of an embodiment of the present invention. Table 1 in the following provides apparatuses for detecting concentration of an oxidizing gas according to the $1^{st}$ to $3^{rd}$ embodiments of the present invention, wherein the photoreducing lights in the $1^{st}$ embodiment and the $2^{nd}$ embodiment have different wavelengths, and the $3^{rd}$ embodiment does not have the photoreducing light.

TABLE 1

|  | $1^{st}$ Embodiment | $2^{nd}$ Embodiment | $3^{rd}$ Embodiment |
|---|---|---|---|
| Metal Oxide | $WO_3$ | $WO_3$ | $WO_3$ |
| Photoreducing light | Ultra Violet Light (wavelength is 365 nanometers) | Fluorescent Lamp | No Light (Darkroom) |

Figure 6:
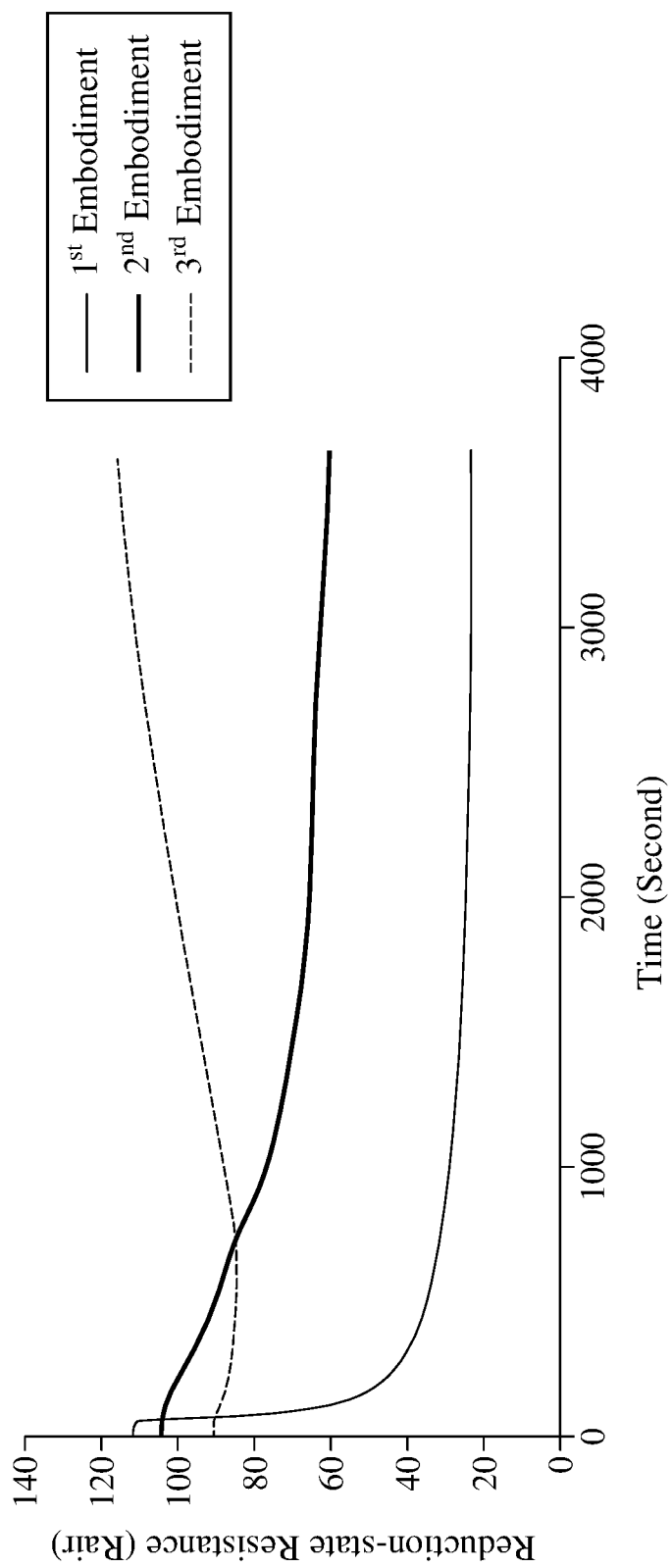
FIG. 6 is a schematic view of the reduction-state resistance obtained by the photoreduction with different lights according to the method for detecting concentration of an oxidizing gas of an embodiment of the present invention.

As shown in FIG. 6, after the step S102 is executed, the reduction-state resistance measured in $1^{st}$ embodiment is smaller, while the reduction-state resistance measured in $2^{nd}$ and $3^{rd}$ embodiment are larger, indicating that after using the photoreducing light to irradiate for the same period of time, the $1^{st}$ embodiment has more metal oxides in oxidation state to be reduced to the reduced state, which means that the reduction speed of the metal oxide in the $1^{st}$ embodiment is faster. However, the present invention is not limited to use the light having a wavelength of 254 nanometers to 430 nanometers to perform the photoreduction reaction of step S102.

In the step S106, the metal oxide 112 can be efficiently oxidized by performing the photocatalysis with the two-color composite light. Please refer to FIG. 7, which is a schematic view of the sensitivity obtained by performing the photocatalytic redox reaction with different lights according to the method for detecting concentration of an oxidizing gas of an embodiment of the present invention. Table 2 in the following provides apparatuses for detecting concentration of an oxidizing gas according to the $4^{th}$ to $7^{th}$ embodiments of the present invention, wherein the light module of embodiment $4^{th}$ comprises two photocatalytic lights with different wavelengths (590 nanometers and 850 nanometers), the light module of embodiment $5^{th}$ to $7^{th}$ comprises a photocatalytic light with a single wavelength. Embodiment $4^{th}$ to $7^{th}$ all perform the step S106 of the method for detecting concentration of an oxidizing gas shown in FIG. 4.

TABLE 2

|  | 4th Embodiment | 5th Embodiment | 6th Embodiment | 7th Embodiment |
| --- | --- | --- | --- | --- |
| Metal Oxide | $WO_3$ | $WO_3$ | $WO_3$ | $WO_3$ |
| Oxidizing Gas | $NO_2$ | $NO_2$ | $NO_2$ | $NO_2$ |
| Concentration of Oxidizing Gas | 1 ppm | 1 ppm | 1 ppm | 1 ppm |
| Photocatalytic Light | Yellow Light (590 nanometers) Near-infrared Light (850 nanometers) | Yellow Light (590 nanometers) | Near-infrared (850 nanometers) | Blue Light (430 nanometers) |

Figure 7:
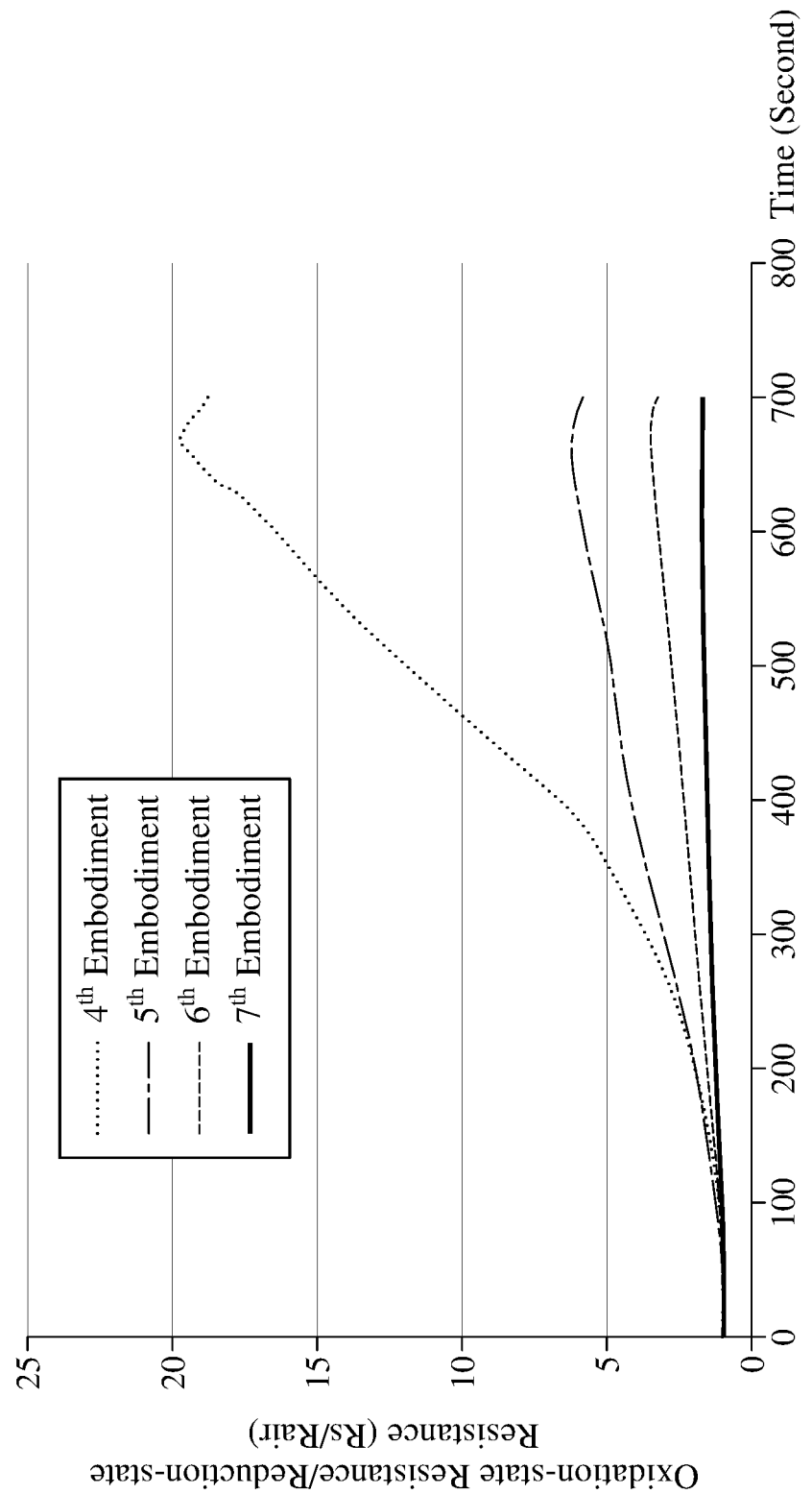
FIG. 7 is a schematic view of the sensitivity obtained by performing the photocatalytic redox reaction with different lights according to the method for detecting concentration of an oxidizing gas of an embodiment of the present invention.

As shown in FIG. 7, after the step S106 is executed, the ratio (Rs/Rair) of the oxidation-state resistance and the reduction-state resistance of the metal oxide measured in $4^{th}$ embodiment is larger, while ratios (Rs/Rair) measured in $5^{th}$ to $7^{th}$ embodiments are smaller, indicating that after using the photocatalytic light(s) to irradiate for the same period of time, the $4^{th}$ embodiment which uses two photocatalytic lights to emit the two-color composite light has more metal oxides in reduction state to react with the oxidizing gas for being oxidized into oxidation state, which means that the reaction rate of the metal oxide and the oxidizing gas in the $4^{th}$ embodiment is faster. However, the present invention is not limited to use the two-color composite light to perform the photocatalysis in step S106.

In the step S106, performing the photocatalysis with the light having a wavelength of 550 nanometers to 950 nanometers can efficiently oxidize the metal oxide 112. Please refer to FIG. 8, which is a schematic view of the reduction-state resistance obtained by performing the photoreduction reaction with different lights according to the method for detecting concentration of an oxidizing gas of an embodiment of the present invention. Table 3 in the following provides apparatuses for detecting concentration of an oxidizing gas according to $8^{th}$ to $11^{th}$ embodiments of the present invention, wherein the light modules of $8^{th}$ to $10^{th}$ embodiments comprises photocatalytic lights with different wavelengths, and $11^{th}$ embodiment does not have the photocatalytic light.

TABLE 3

|  | 8th Embodiment | 9th Embodiment | 10th Embodiment | 11th Embodiment |
| --- | --- | --- | --- | --- |
| Metal Oxide | $WO_3$ | $WO_3$ | $WO_3$ | $WO_3$ |
| Oxidizing Gas | $NO_2$ | $NO_2$ | $NO_2$ | $NO_2$ |
| Concentration of Oxidizing Gas | 1 ppm | 1 ppm | 1 ppm | 1 ppm |
| Photocatalytic Light | Yellow Light (590 nanometers) Near-infrared Light (850 nanometers) | Yellow Light (590 nanometers) | Fluorescent Lamp | No Light (Darkroom) |

Figure 8:
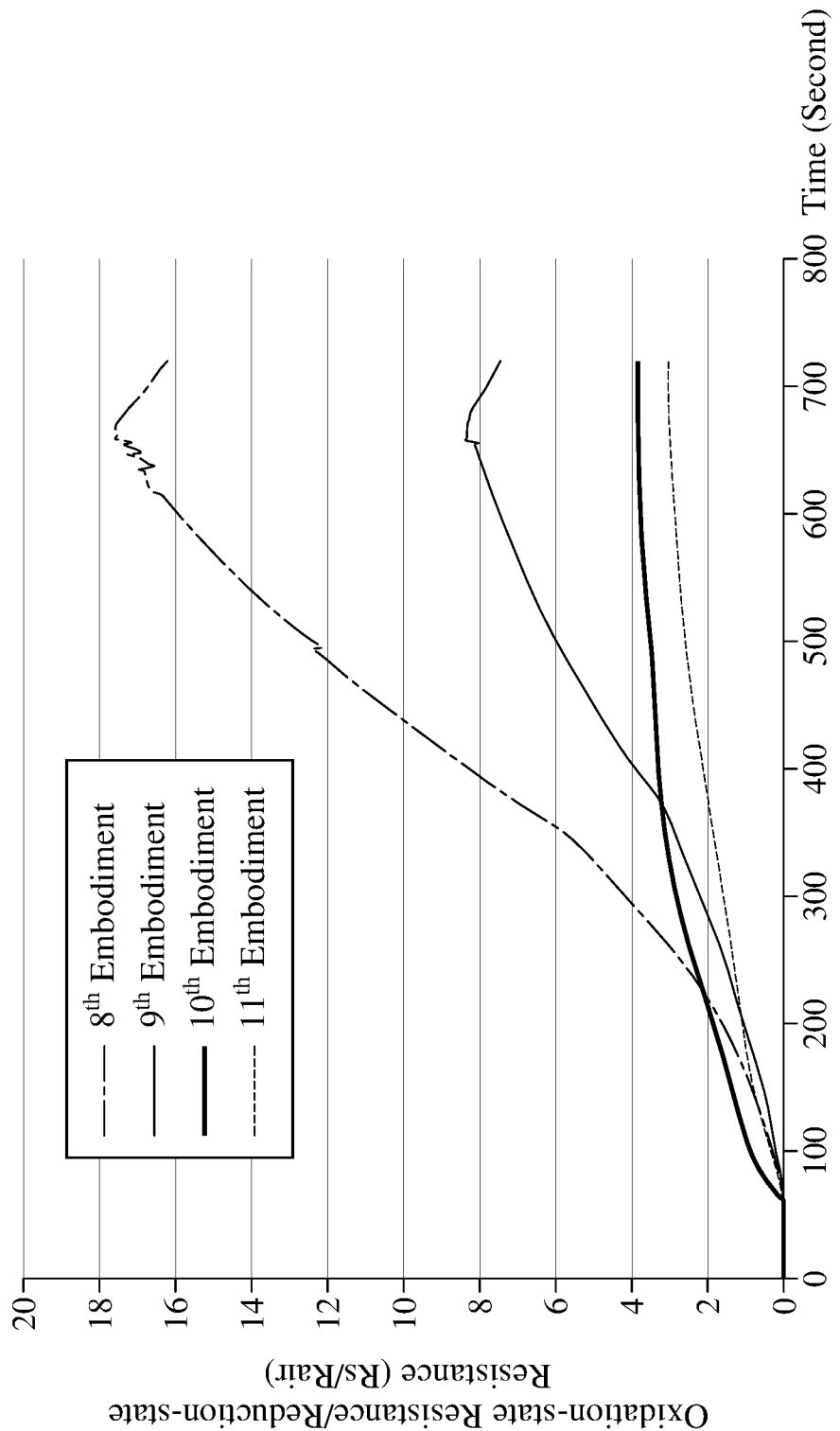
FIG. 8 is a schematic view of the reduction-state resistance obtained by performing the photoreduction reaction with different lights according to the method for detecting concentration of an oxidizing gas of an embodiment of the present invention.

As shown in FIG. 8, after the step S106 is executed, the ratios (Rs/Rair) of the oxidation-state resistance and the reduction-state resistance of the metal oxide measured in the $8^{th}$ embodiment and the 9th embodiment are larger, while ratios measured in $10^{th}$ to $11^{th}$ embodiments are smaller, indicating that after using the photocatalytic light(s) to irradiate for the same period of time, the $8^{th}$ embodiment and the 9th embodiment which are irradiated by the lights with a wavelength of 550 nanometers 990 nanometers have more metal oxides in reduction state to react with the oxidizing gas for being oxidized into oxidation state, which means that the reaction rates of the metal oxide and the oxidizing gas in the $8^{th}$ embodiment and the $9^{th}$ embodiment are faster. However, the present invention is not limited to use the light with a wavelength of 550 nanometers 990 nanometers to perform the photocatalysis in step S106.

Figure 9:
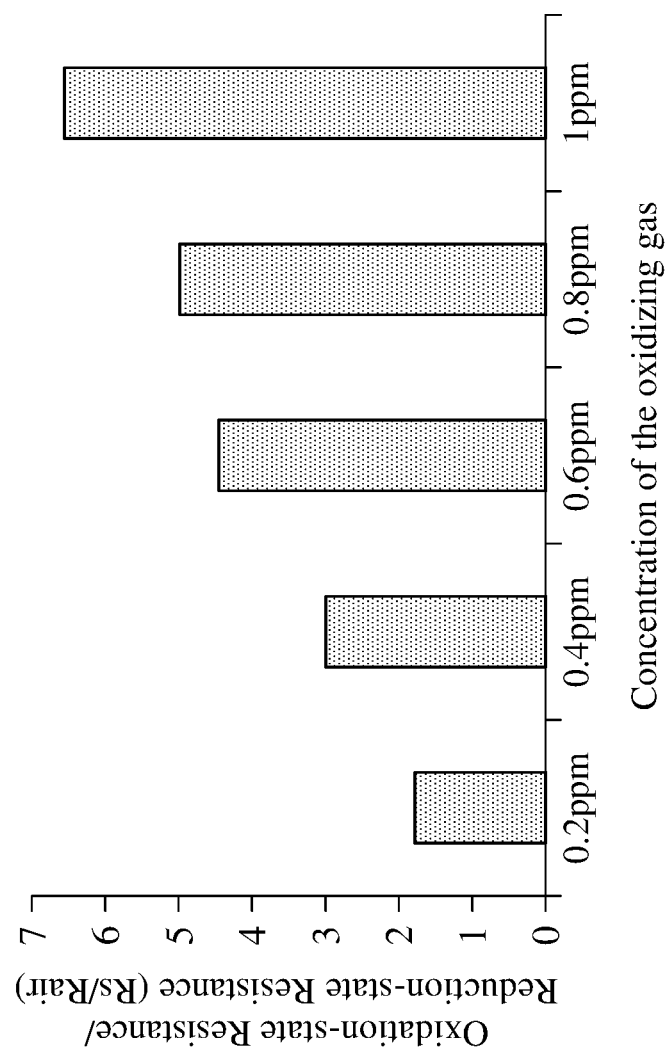
FIG. 9 is a schematic view of the sensitivity of different concentrations of oxidizing gas according to the method for detecting concentration of an oxidizing gas of an embodiment of the present invention.

The method for detecting concentration of an oxidizing gas and the apparatus for detecting concentration of an oxidizing gas of the present invention have a high sensibility to apply for the detection of the oxidizing gas with low concentration. Please refer to FIG. 9, which is a schematic view of the sensitivity of different concentrations of oxidizing gas according to the method for detecting concentration of an oxidizing gas of an embodiment of the present invention. Even the oxidizing gas with extremely low concentration (0.2 ppm to 1 ppm) reacts with the metal oxide, the ratio (Rs/Rair) of the oxidation-state resistance and the reduction-state resistance obtained by adopting the method for detecting concentration of an oxidizing gas and the apparatus for detecting concentration of an oxidizing gas of the present invention is large enough.

Figure 10:
FIG. 10 is a schematic view of the relative sensitivity under the interferences of different interference gases according to the method for detecting concentration of an oxidizing gas of an embodiment of the present invention and the method for detecting concentration of an oxidizing gas of the comparative example.

The method for detecting concentration of an oxidizing gas according to the present invention adopts photocatalysis to oxidize the metal oxide, so the detection result of the concentration of the oxidizing gas is not easily interfered by the reducing gas. Please refer to FIG. 10, which is a schematic view of the relative sensitivity under the interferences of different interference gases according to the method for detecting concentration of an oxidizing gas of an embodiment of the present invention and the method for detecting concentration of an oxidizing gas of the comparative example. As set forth above, the method for detecting concentration of an oxidizing gas of the comparative example is a conventional method to let the metal oxide react with the oxidizing gas by heating. As shown in FIG. 10, when detecting the oxidizing gas ($NO_2$), the embodiments of the present invention and the comparative example have similar relative sensitivity, that is, both the embodiments of the present invention and the comparative example can accurately detect the concentration of the oxidizing gas. However, when detecting the gas mixture comprising oxidizing gas and reducing gas (such as hydrogen, argon, alcohol gas), the comparative example has a higher relative sensitivity to the reducing gas and is therefore susceptible to the interference of the reducing gas to give a wrong resistance value of the metal oxide, furthermore, the concentration of the oxidizing gas detected differs from the actual concentration.

The apparatus for detecting concentration of an oxidizing gas comprises a nano-metal catalyst layer configured to catalyze the oxidizing gas and the metal oxide to perform the redox reaction, further improving the efficiency of the redox reaction. Please refer to FIG. 11, which is a schematic view showing the result of operating the apparatus for detecting concentration of an oxidizing gas according to the embodiment of the present invention and the comparative example for detecting concentration of oxidizing gas according to the method for detecting concentration of oxidizing gas according to an embodiment of the present invention. Table 4 in the following provides apparatuses for detecting concentration of an oxidizing gas according to $12^{th}$ embodiment and $13^{th}$ embodiment of the present invention, wherein gas detecting module of the $12^{th}$ embodiment comprises a nano-silver-metal catalyst layer and the gas detecting module of the $13^{th}$ embodiment does not have the nano-metal catalyst layer. The 12$^{th}$ embodiment and the 13$^{th}$ embodiment all perform the method for detecting concentration of an oxidizing gas shown in FIG. 4.

TABLE 4

|  | 12$^{th}$ Embodiment | 13$^{th}$ Embodiment |
| --- | --- | --- |
| Metal Oxide Nanoconductor | WO$_3$ Nanocarbon Material | WO$_3$ Nanocarbon Material |
| Nano-Metal Catalyst Layer | Silver | None |
| Oxidizing Gas | NO$_2$ | NO$_2$ |
| Concentration of the Oxidizing Gas | 1 ppm | 1 ppm |
| Photocatalytic Light | Yellow Light (590 nanometers) Near-Infrared Light (850 nanometers) | Yellow Light (590 nanometers) Near-Infrared Light (850 nanometers) |

Figure 11:
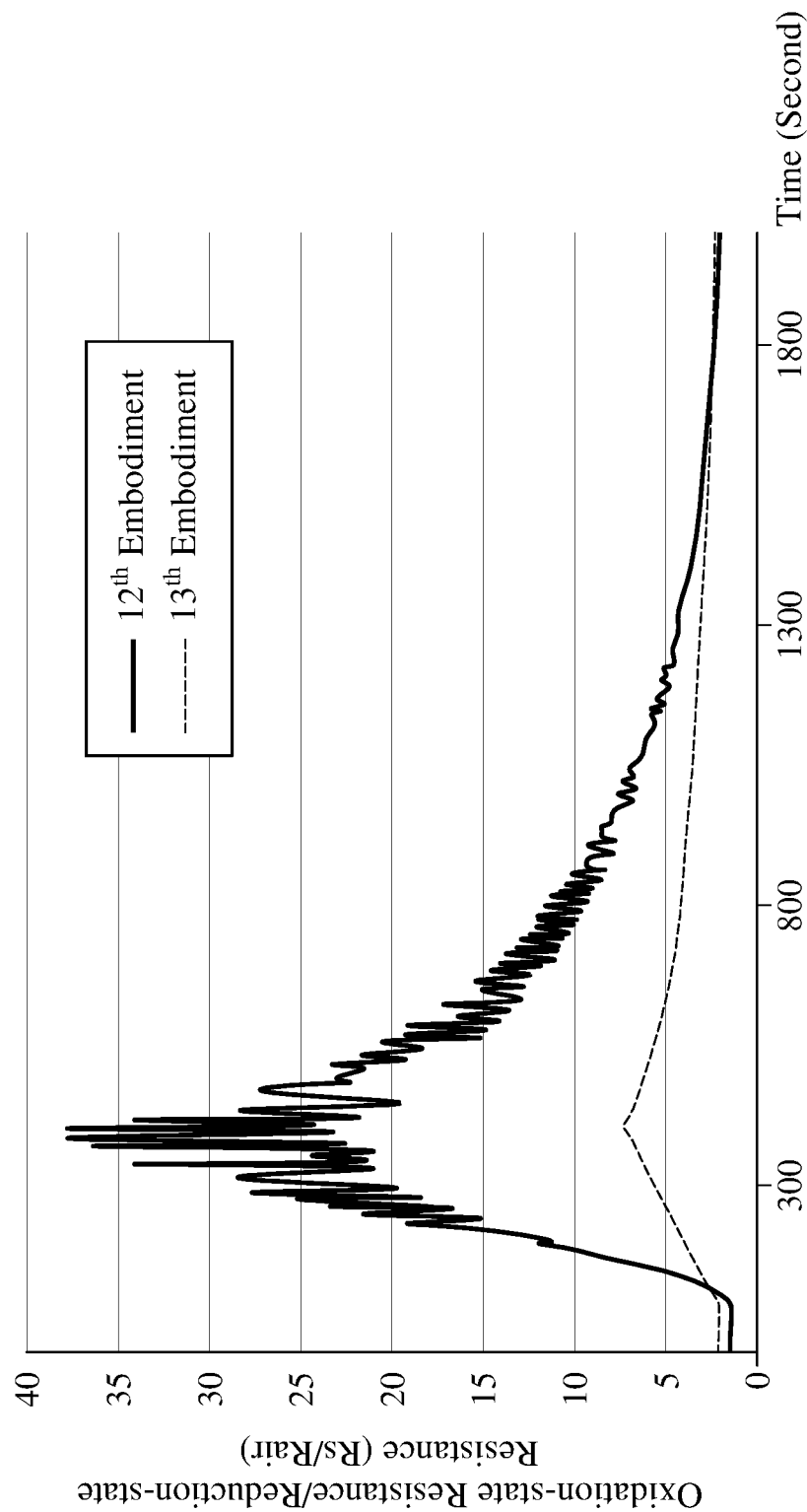
FIG. 11 is a schematic view showing the result of operating the apparatus for detecting concentration of an oxidizing gas according to the embodiment of the present invention and the comparative example for detecting concentration of oxidizing gas according to the method for detecting concentration of oxidizing gas according to an embodiment of the present invention.

As shown in FIG. 11, the ratio (Rs/Rair) of the oxidation-state resistance and the reduction-state resistance of the metal oxide measured in 12$^{th}$ embodiment is larger, indicating that after using the photocatalytic lights to irradiate for the same period of time, the 12$^{th}$ embodiment which comprises the nano-metal catalyst layer has more metal oxides in reduction state to react with the oxidizing gas for being oxidized into oxidation state, which means that the reaction rate of the metal oxide and the oxidizing gas in the 12$^{th}$ embodiment is faster. However, the present invention is not limited to the gas detecting module with the nano-metal catalyst layer.

The nano-metal catalyst layer of the apparatus for detecting concentration of an oxidizing gas according to an embodiment of the present invention is a mixture of gold/silver, with better catalytic effect than gold, silver or palladium. Please refer to FIG. 12, which is a schematic view showing the detection result performed according to the method for detecting concentration of an oxidizing gas of an embodiment of the present invention by the apparatuses for detecting concentration of an oxidizing gas according to the different embodiments of the present invention. Table 5 in the following provides apparatuses for detecting concentration of an oxidizing gas according to 14$^{th}$ embodiment to 16$^{th}$ embodiment of the present invention, wherein the gas detecting module of the 14$^{th}$ embodiment comprises metal catalyst layer of a mixture of nano-gold/nano-silver, the gas detecting module of the 15$^{th}$ embodiment comprises the nano-silver-metal catalyst layer, and the gas detecting module of the 16$^{th}$ embodiment comprises the nano-gold-metal catalyst layer. 14$^{th}$-16$^{th}$ embodiments all perform the method for detecting concentration of oxidizing gas shown in FIG. 4.

TABLE 5

|  | 14$^{th}$ Embodiment | 15$^{th}$ Embodiment | 16$^{th}$ Embodiment |
| --- | --- | --- | --- |
| Metal Oxide Nanoconductor | WO$_3$ Nanocarbon Material | WO$_3$ Nanocarbon Material | WO$_3$ Nanocarbon Material |
| Nano-Metal Catalyst Layer | Mixture of Gold/Silver | Silver | Gold |
| Oxidizing Gas | NO$_2$ | NO$_2$ | NO$_2$ |
| Concentration of Oxidizing Gas | 1 ppm | 1 ppm | 1 ppm |
| Photocatalytic Light | Yellow Light (590 nanometers) Near-Infrared Light (850 nanometers) | Yellow Light (590 nanometers) Near-Infrared Light (850 nanometers) | Yellow Light (590 nanometers) Near-Infrared Light (850 nanometers) |

Figure 12:
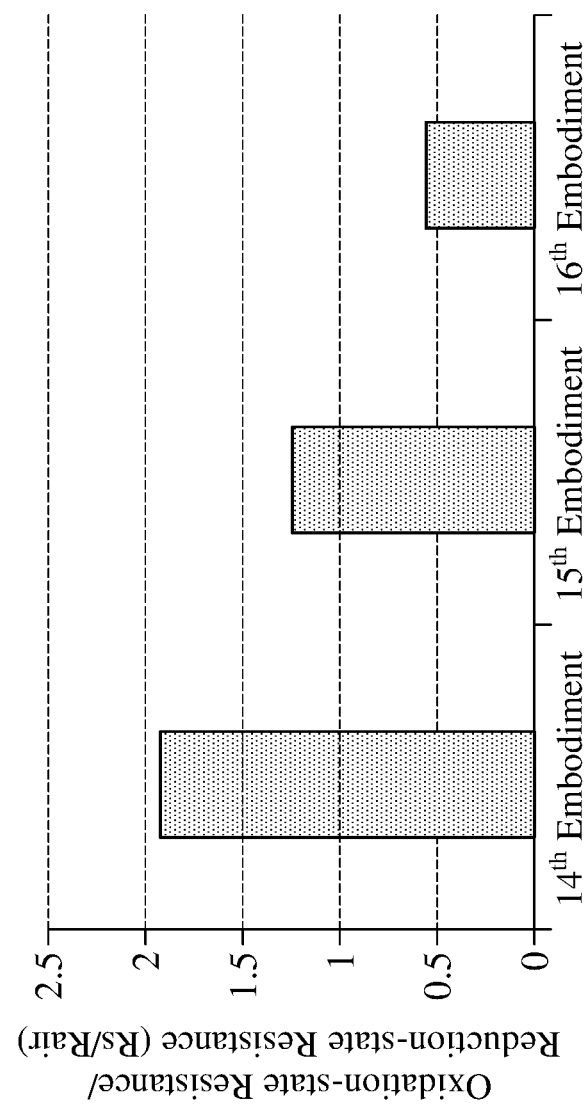
FIG. 12 is a schematic view showing the detection result performed according to the method for detecting concentration of an oxidizing gas of an embodiment of the present invention by the apparatuses for detecting concentration of an oxidizing gas according to the different embodiments of the present invention.

As shown in FIG. 12, the ratio (Rs/Rair) of the oxidation-state resistance and the reduction-state resistance of the metal oxide measured in 14$^{th}$ embodiment is larger, indicating that after using the photocatalytic lights to irradiate for the same period of time, the 14$^{th}$ embodiment which comprises the nano-metal catalyst layer with the mixture of gold/silver has more metal oxides in reduction state to react with the oxidizing gas for being oxidized into oxidation state, which means that the reaction rate of the metal oxide and the oxidizing gas in the 14$^{th}$ embodiment is faster. The reaction rate of the 14$^{th}$ embodiment with nano-metal catalyst later having silver is second faster. However, the present invention is not limited to the nano-metal catalyst layer with the mixture of gold/silver.

As set forth above, according to the method for detecting concentration of an oxidizing gas and the apparatus thereof, by firstly performing an electroreduction reaction and a photoreduction reaction simultaneously to the metal oxide; then stopping the electroreduction reaction and the photoreduction reaction to the metal oxide; then applying a first pulse-width modulation signal for reading an reduction-state resistance of the reduced metal oxide; then providing the oxidizing gas to the reduced metal oxide; then performing a redox reaction by photo-catalyzing the oxidizing gas and the reduced metal oxide; then applying a second pulse-width modulation signal for reading an oxidation-state resistance of the oxidized metal oxide, the sensitivity of the method for detecting concentration of an oxidizing gas is improved. Moreover, through performing a redox reaction by photo-catalyzing the oxidizing gas and the reduced metal oxide, the detection result of the concentration of the oxidizing gas is not easily interfered by the reducing gas. In this way, the method for detecting concentration of an oxidizing gas and apparatus thereof as set forth above can satisfy the requirement of real-time monitoring of the concentration of trace oxidizing gas, and can solve the problem that the detection result is easily interfered by the reducing gas.

Although the aforementioned embodiments of this invention have been described above, this invention is not limited thereto. The amendment and the retouch, which do not depart from the spirit and scope of this invention, should fall within the scope of protection of this invention. For the scope of protection defined by this invention, please refer to the attached claims.

| SYMBOLIC EXPLANATION | |
| --- | --- |
| 1 | apparatus for detecting concentration of the oxidizing gas |
| 110 | gas detecting module |
| 111 | substrate |
| 112 | metal oxide |
| 113 | nanoconductor |
| 114 | first electrode |
| 115 | second electrode |
| 116 | nano-metal catalyst layer |
| 120 | light module |
| 121 | photoreducing light |

-continued

| | SYMBOLIC EXPLANATION |
|---|---|
| 122 | photocatalytic light |
| 123 | photocatalytic light |
| 130 | control module |
| 131 | pulse-width modulator |
| 132 | first voltage regulator |
| 133 | second voltage regulator |
| 134 | controller |
| 140 | casing |
| S101~S108 | steps |
| P | power source |
| W1 | first pulse-width modulation signal |
| W2 | second pulse-width modulation signal |
| Rair | reduction-state resistance |
| Rs | oxidation-state resistance |

What is claimed is:

1. A method for detecting concentration of an oxidizing gas comprising:
providing a gas detecting module with the gas detecting module comprising a metal oxide and a plurality of nanoconductors, wherein the plurality of nanoconductors are distributed in the metal oxide;
performing an electroreduction reaction and a photoreduction reaction simultaneously to the metal oxide;
stopping the electroreduction reaction and the photoreduction reaction to the metal oxide;
applying a first pulse-width modulation signal for reading a reduction-state resistance of a reduced metal oxide;
providing the oxidizing gas to the reduced metal oxide;
performing a redox reaction by photo-catalyzing the oxidizing gas and the reduced metal oxide;
applying a second pulse-width modulation signal for reading an oxidation-state resistance of the oxidized metal oxide; and
calculating the concentration of the oxidizing gas according to a ratio of the oxidation-state resistance to the reduction-state resistance.

2. The method for detecting concentration of an oxidizing gas according to claim 1, wherein performing the electroreduction reaction to the metal oxide is to apply a voltage of 5 to 10 volts to the metal oxide.

3. The method for detecting concentration of an oxidizing gas according to claim 1, wherein performing the photoreduction reaction to the metal oxide is to irradiate the metal oxide with a light with a wavelength of 254 to 430 nanometers.

4. The method for detecting concentration of an oxidizing gas according to claim 1, wherein a time for performing the electroreduction reaction and the photoreduction reaction simultaneously to the metal oxide is 0.1 to 5 minutes.

5. The method for detecting concentration of an oxidizing gas according to claim 1, wherein a step of stopping the electroreduction reaction and the photoreduction reaction to the metal oxide is to stop performing the photoreduction reaction firstly, then to stop performing the electroreduction reaction after 0.1 to 5 minutes.

6. The method for detecting concentration of an oxidizing gas according to claim 1, wherein the first pulse-width modulation signal is a pulse-width modulation signal with voltage ranging from 3 to 7 volts and with frequency ranging from 5 to 15 hertz.

7. The method for detecting concentration of an oxidizing gas according to claim 1, wherein time for applying the first pulse-width modulation signal is 0.1 to 1000 milliseconds.

8. The method for detecting concentration of an oxidizing gas according to claim 1, wherein a step of performing the redox reaction by photo-catalyzing the oxidizing gas and the reduced metal oxide is to apply a monochromatic light with a wavelength of 550 to 950 nanometers to irradiate a contact surface of the reduced metal oxide and the oxidizing gas.

9. The method for detecting concentration of an oxidizing gas according to claim 1, wherein a step of performing the redox reaction by photo-catalyzing the oxidizing gas and the reduced metal oxide is to apply a two-color composite light with a wavelength of 550 to 950 nanometers to irradiate a contact surface of the reduced metal oxide and the oxidizing gas.

10. The method for detecting concentration of an oxidizing gas according to claim 1, wherein the second pulse-width modulation signal is a pulse-width modulation signal with voltage ranging from 3 to 7 volts and with frequency ranging from 5 to 15 hertz.

11. The method for detecting concentration of an oxidizing gas according to claim 1, wherein a time for applying the second pulse-width modulation signal is 0.1 to 1000 milliseconds.

12. The method for detecting concentration of an oxidizing gas according to claim 1, wherein the oxidizing gas is nitrogen dioxide or ozone.

13. The method for detecting concentration of an oxidizing gas according to claim 1, wherein a step of performing the redox reaction by photo-catalyzing the oxidizing gas and the reduced metal oxide is performed at room temperature.

14. An apparatus for detecting concentration of an oxidizing gas comprising:
a gas detecting module comprising a metal oxide and a plurality of nanoconductors, wherein the plurality of nanoconductors are distributed in the metal oxide, and the metal oxide is configured to perform a redox reaction with the oxidizing gas;
a light module comprising a photoreducing light and at least one photocatalytic light, wherein the photoreducing light is configured to irradiate and drive the metal oxide to be photoreduced, and said at least one photocatalytic light is configured to catalyze a reaction of the oxidizing gas with a reduced metal oxide so that the oxidizing gas is reduced; and
a control module electrically connected to the gas detecting module and the light module, wherein the control module is configured to drive the metal oxide to be electroreduced and photoreduced in a constant voltage mode, and to detect a reduction-state resistance of the reduced metal oxide and an oxidation-state resistance of the oxidized metal oxide in a pulse-width modulation mode, wherein the reduction-state resistance and the oxidation-state resistance are configured to calculate a concentration of the oxidizing gas.

15. The apparatus for detecting concentration of an oxidizing gas according to claim 14, wherein the control module comprises a pulse-width modulator and a controller, the gas detecting module electrically connects to a power source through the controller in the constant voltage mode, and the gas detecting module electrically connects to the power source through the controller and the pulse-width modulator in the pulse-width modulation mode.

16. The apparatus for detecting concentration of an oxidizing gas according to claim 15, wherein the gas detecting module further comprises a first electrode and a second electrode, the metal oxide only electrically connects to the first electrode and the second electrode directly, and the first electrode electrically connects to the controller.

17. The apparatus for detecting concentration of an oxidizing gas according to claim 14, wherein the photoreducing light is a light source with a wavelength of 254 to 430 nanometers, and said at least one photocatalytic light is a light source with a wavelength of 550 to 950 nanometers.

18. The apparatus for detecting concentration of an oxidizing gas according to claim 17, wherein said at least one photocatalytic light comprises two photocatalytic lights with different wavelengths.

19. The apparatus for detecting concentration of an oxidizing gas according to claim 14, wherein the photoreducing light is a light source with a wavelength of 365 nanometers, and the photocatalytic light comprises a near-infrared light source with a wavelength of 850 nanometers and a visible light source with a wavelength of 950 nanometers.

20. The apparatus for detecting concentration of an oxidizing gas according to claim 14, wherein the metal oxide is tungsten trioxide or titanium dioxide.

21. The apparatus for detecting concentration of an oxidizing gas according to claim 14, wherein the plurality of nanoconductors is carbon nanotube, graphene, polyacetylene, polythiophene (PT), polypyrrole (PPY), polyaniline (PANI) or poly(3,4 ethylenedioxythiophene)-poly(styrenesulfonate) (PEDOT-PSS).

22. The apparatus for detecting concentration of an oxidizing gas according to claim 14, wherein the gas detecting module further comprises a nano-metal catalyst layer, the nano-metal catalyst layer is disposed on a surface of the metal oxide, the nano-metal catalyst layer is configured to catalyze the oxidizing gas and the metal oxide to perform a redox reaction.

23. The apparatus for detecting concentration of an oxidizing gas according to claim 22, wherein a material of the nano-metal catalyst layer is gold, silver or palladium.

24. The apparatus for detecting concentration of an oxidizing gas according to claim 23, wherein a material of the nano-metal catalyst layer is a mixture of gold and silver.

* * * * *